(12) United States Patent
Nemati et al.

(10) Patent No.: US 12,350,019 B2
(45) Date of Patent: Jul. 8, 2025

(54) METHODS AND SYSTEMS FOR DETERMINING ABNORMAL CARDIAC ACTIVITY

(71) Applicants: Emory University, Atlanta, GA (US); Georgia Tech Research Corporation, Atlanta, GA (US)

(72) Inventors: Shamim Nemati, Atlanta, GA (US); Gari Clifford, Atlanta, GA (US); Supreeth Prajwal Shashikumar, Atlanta, GA (US); Amit Jasvant Shah, Atlanta, GA (US); Qiao Li, Atlanta, GA (US)

(73) Assignee: Emory University, Atlanta, GA (US)

( * ) Notice: Subject to any disclaimer, the term of this patent is extended or adjusted under 35 U.S.C. 154(b) by 474 days.

(21) Appl. No.: 17/571,298

(22) Filed: Jan. 7, 2022

(65) Prior Publication Data
US 2022/0125322 A1 Apr. 28, 2022

Related U.S. Application Data

(63) Continuation of application No. 16/472,818, filed as application No. PCT/US2017/068029 on Dec. 21, 2017, now abandoned.
(Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/7221* (2013.01); *A61B 5/7253* (2013.01);
(Continued)

(58) Field of Classification Search
CPC ... A61B 5/0205; A61B 5/7221; A61B 5/7253; A61B 5/7267; G16H 10/60; G16H 50/20
See application file for complete search history.

(56) References Cited

U.S. PATENT DOCUMENTS 9,113,830 B2 8/2015 Galen et al.
9,420,956 B2 8/2016 Gopalakrishnan et al.
(Continued)

FOREIGN PATENT DOCUMENTS

EP 1 724 684 A1 11/2006
WO WO 2008/007236 A2 1/2008
(Continued)

OTHER PUBLICATIONS

Bahdanau et al. "Neural Machine Translation By Jointly Learning To Align And Translate." Paper presented at 3rd International Conference on Learning Representations. ICLR 2015, San Diego, United States. 2015; 1-15.
(Continued)

*Primary Examiner* — Christopher A Flory
(74) *Attorney, Agent, or Firm* — Emory Patent Group (57) ABSTRACT

The systems and methods can accurately and efficiently determine abnormal cardiac activity from motion data and/or cardiac data using techniques that can be used for long-term monitoring of a patient. In some embodiments, the method for using machine learning to determine abnormal cardiac activity may include receiving one or more periods of time of cardiac data and motion data for a subject. The method may include applying a trained deep learning architecture to each tensor of the one or more periods of time to classify each window and/or each period into one or more classes using at least the one or more signal quality indices for the cardiac data and the motion data and cardiovascular features. The deep learning architecture may include a convolutional neural network, a bidirectional recurrent neu- (Continued)

ral network, and an attention network. The one or more classes may include abnormal cardiac activity and normal cardiac activity.

20 Claims, 7 Drawing Sheets

Related U.S. Application Data (60) Provisional application No. 62/437,457, filed on Dec. 21, 2016.

(51) Int. Cl.
   *G16H 10/60* (2018.01)
   *G16H 50/20* (2018.01)

(52) U.S. Cl.
   CPC ........... *A61B 5/7267* (2013.01); *G16H 10/60* (2018.01); *G16H 50/20* (2018.01)

(56) References Cited

U.S. PATENT DOCUMENTS

| | | | |
|---|---|---|---|
| 10,779,744 | B2 | 9/2020 | Rapin et al. |
| 2005/0065569 | A1 | 3/2005 | Ricci et al. |
| 2008/0013747 | A1 | 1/2008 | Tran |
| 2009/0259133 | A1* | 10/2009 | Wolfberg ............... A61B 5/412 600/511 |
| 2012/0016209 | A1 | 1/2012 | Wolfberg et al. |
| 2012/0083676 | A1 | 4/2012 | Wolfberg et al. |
| 2012/0123232 | A1 | 5/2012 | Najarian et al. |
| 2015/0164349 | A1 | 6/2015 | Gopalakrishnan et al. |
| 2016/0199215 | A1 | 7/2016 | Kopelman |
| 2017/0249445 | A1* | 8/2017 | Devries ................. A61B 5/145 |
| 2017/0360412 | A1* | 12/2017 | Rothberg ............. A61B 8/5207 |
| 2018/0108440 | A1* | 4/2018 | Stevens ................. G06N 3/044 |
| 2018/0172694 | A1* | 6/2018 | Farokhzad ....... G01N 33/57488 |
| 2019/0034590 | A1* | 1/2019 | Oren ...................... G06N 3/044 |
| 2019/0110754 | A1* | 4/2019 | Rao .......................... G06N 7/00 |
| 2019/0223739 | A1 | 7/2019 | Rapin et al. |
| 2019/0374166 | A1* | 12/2019 | Charles ................ A61B 5/0006 |
| 2020/0085312 | A1* | 3/2020 | Tzvieli ............... A61B 5/02055 |
| 2020/0085333 | A1* | 3/2020 | Freed ................... A61B 5/7264 |
| 2020/0260979 | A1* | 8/2020 | Cao ........................ A61B 5/358 |
| 2020/0260980 | A1* | 8/2020 | Liu ........................ A61B 5/352 |
| 2020/0289094 | A1 | 9/2020 | de Jonge et al. |
| 2020/0305799 | A1* | 10/2020 | Cao ........................ A61B 5/355 |

FOREIGN PATENT DOCUMENTS

| | | |
|---|---|---|
| WO | WO 2012/166769 A1 | 12/2012 |
| WO | WO 2016/038585 A1 | 3/2016 |
| WO | WO 2016/170005 A1 | 10/2016 |
| WO | WO 2017/117798 A1 | 7/2017 |

OTHER PUBLICATIONS

Choi et al. "RETAIN: An Interpretable Predictive Model for Healthcare using Reverse Time Attention Mechanism." Proceedings of Neural Information Processing Systems. 2016; 3512-3520.
Choi et al. "GRAM: Graph-based Attention Model for Healthcare Representation Learning." KDD: proceedings. International Conference on Knowledge Discovery & Data Mining. 2017; 787-795.
Chowdhury et al. "Real-Time Robust Heart Rate Estimation From Wrist-Type PPG Signals Using Multiple Reference Adaptive Noise Cancellation." IEEE Journal of Biomedical and Health Informatics. 2018; 22(2): 450-459.
Crisci et al. "A review of supervised machine learning algorithms and their applications to ecological data." Ecological Modeling. 2012; 240: 113-122.
Ferranti et al. "Atrial Fibrillation detection in PPG signal recorded through a wristband device." Politecnico Di Milano. 2015.
Kiranyaz et al. "Real-Time Patient Specific ECG Classification by 1-D Convolutional Neural Networks." IEEE Transactions on Biomedical Engineering. 2016; 63(3): 664-675.
Nemati et al. "Monitoring and Detecting Atrial Fibrillation using Wearable Technology." Annual International Conference of the IEEE Engineering in Medicine and Biology Society. 2016; 3394-3397.
Shashikumar et al. "A Deep Learning Approach to Monitoring and Detecting Atrial Fibrillation using Wearable Technology." 2017 IEEE EMBS International Conference on Biomedical & Health Informatics (BHI), Orlando, FL, USA. 2017; 141-144.
Stankevicius et al. "Photoplethysmography-Based System for Atrial Fibrillation Detection During Hemodialysis." In: Kyriacou, E. et al. (eds), XIV Mediterranean Conference on Medical and Biological Engineering and Computing 2016. IFMBE Proceedings. 2016; 57: 79-80.
Vaswani et al. "Attention is All You Need." NIPS '17: Proceedings of the 31st International Conference on Neural Information Processing Systems. 2017; 6000-6010.
Extended European Search Report for EP Application No. 17882641.8 dated Jul. 20, 2020.
Extended European Search Report for EP Application No. 21174720.9 dated Sep. 20, 2021.
International Search Report and Written Opinion for PCT Application No. PCT/US2017/068029 dated Feb. 22, 2018.
Non-Final Office Action for U.S. Appl. No. 16/472,818 mailed Jul. 7, 2021.

* cited by examiner

Wavelet Transform

AF     NSR

METHODS AND SYSTEMS FOR DETERMINING ABNORMAL CARDIAC ACTIVITY

CROSS-REFERENCE TO RELATED APPLICATIONS

This application is a continuation of U.S. application Ser. No. 16/472,818 filed Jun. 21, 2019, which is the National Stage of International Application No. PCT/US2017/068029 filed Dec. 21, 2017, which claims the benefit of U.S. Provisional Application No. 62/437,457 filed Dec. 21, 2016. The entirety of these applications is hereby incorporated by reference for all purposes.

BACKGROUND

Arrhythmias, which are characterized by abnormal heart rates, can cause fatal conditions, such as strokes or sudden cardiac death, as well as be an indicator of a serious condition, such as heart disease. One of the most common form arrhythmia is atrial fibrillation (Afib).

Generally, arrhythmias are detected from continuous ECG (electrocardiographic) monitoring using ECG devices that are used periodically over a few weeks. These monitoring techniques can require the use of multiple electrodes, for example, patches and implantable devices, making them cumbersome and sometimes invasive for the user. These techniques can also be costly, although being used for short-term. Further, many patients or subjects suffering from atrial fibrillation (Afib) can be asymptomatic and the ECG monitoring may not detect unknown Afib. Thus, current ECG methods and devices can also be inefficient in detecting Afib.

There has been some developments in using wearable devices that detect photoplethysmogram (PPG) data. However, PPG recordings can be noisy due to movement of the user and the noisy recordings can mask occurrences of Afib.

SUMMARY

Thus, there is need for systems and methods that provide a cost effective, accurate detection of abnormal cardiac activity and that can be used for long-term monitoring.

The disclosure relates to systems and methods that can accurately determine abnormal cardiac activity of a subject using a deep learning architecture.

In some embodiments, the methods may include computer-implemented method for using machine learning to determine abnormal cardiac activity of a subject. The method may include receiving one or more periods of time of cardiac data and motion data for a subject. Each period of time including more than one window of the cardiac data and the motion data. The method may further include determining one or more signal quality indices for each window of the cardiac data and the motion data of the one or more periods of time. The method may also include extracting one or more cardiovascular features for each period of time using at least the cardiac data, the motion data, and the one or more signal quality indices for the cardiac data and the motion data. The method may include applying a tensor transform to the cardiac data and/or the motion data to generate a tensor for each window of the one or more periods of time. The method may also include applying a trained deep learning architecture to each tensor of the one or more periods of time to classify each window and/or each period into one or more classes using at least the one or more signal quality indices for the cardiac data and the motion data and cardiovascular features. In some embodiments, the deep learning architecture may include a convolutional neural network, a bidirectional recurrent neural network, and an attention network. The one or more classes may include abnormal cardiac activity and normal cardiac activity. The method may further include generating a report including a classification of cardiac activity of the subject for the one or more periods based on the one or more classes.

In some embodiments, the method may further include receiving subject contextual information for the subject. The subject contextual information may include medical history and demographic information. The extracting may use one or more subject information features related to the subject contextual information to extract one or more cardiovascular features for each period of time, and the trained deep learning architecture may use the one or more subject information features to classify the cardiac activity for each window of the period.

In some embodiments, the tensor transform may be applied to the cardiac data and the motion data for each window.

In some embodiments, the method may further include determining a quality channel for each window based on the one or more signal quality indices for the cardiac data and the motion data. The quality channel may correspond to a channel in each window having the one more quality indices that is higher than remaining channels in each channel.

In some embodiments, the applying the deep learning architecture may include encoding each tensor for each window of the one or more periods using the deep convolutional network into one or more deep learning features associated with cardiac activity. The applying may also include applying the bidirectional recurrent network to determine a probability that each window of the one or more periods belongs to a class of the one or more classes. The bidirectional recurrent network may use the one or more deep learning features, the one more signal quality indices for the cardiac data and/or motion data, and/or one or more cardiovascular features to classify each window of the one or more periods. The applying may also include determining the classification of cardiac activity for each window of the one or more periods and/or each period by applying the attention network to the probability for each window of the one or more periods.

In some embodiments, the attention network may determine a score for each window and/or each period, the score representing the classification of cardiac activity. In some embodiments, when the classification of cardiac activity includes abnormal cardiac activity, a window of each period having a highest score may represent the window including the abnormal cardiac activity.

In some embodiments, the computer readable media may include a non-transitory computer-readable storage medium storing instructions for using machine learning to determine abnormal cardiac activity of a subject. The instructions may include receiving one or more periods of time of cardiac data and motion data for a subject. Each period of time including more than one window of the cardiac data and the motion data. The instructions may further include determining one or more signal quality indices for each window of the cardiac data and the motion data of the one or more periods of time. The instructions may also include extracting one or more cardiovascular features for each period of time using at least the cardiac data, the motion data, and the one or more signal quality indices for the cardiac data and the motion data. The instructions may include applying a tensor transform to the cardiac data and/or the motion data to generate a tensor for each window of the one or more periods of time. The instructions may also include applying a trained deep learning architecture to each tensor of the one or more periods of time to classify each window and/or each period into one or more classes using at least the one or more signal quality indices for the cardiac data and the motion data and cardiovascular features. In some embodiments, the deep learning architecture may include a convolutional neural network, a bidirectional recurrent neural network, and an attention network. The one or more classes may include abnormal cardiac activity and normal cardiac activity. The instructions may further include generating a report including a classification of cardiac activity of the subject for the one or more periods based on the one or more classes.

In some embodiments, the instructions may further include receiving subject contextual information for the subject. The subject contextual information may include medical history and demographic information. The extracting may use one or more subject information features related to the subject contextual information to extract one or more cardiovascular features for each period of time, and the trained deep learning architecture may use the one or more subject information features to classify the cardiac activity for each window of the period.

In some embodiments, the tensor transform may be applied to the cardiac data and the motion data for each window.

In some embodiments, the instructions may further include determining a quality channel for each window based on the one or more signal quality indices for the cardiac data and the motion data. The quality channel may correspond to a channel in each window having the one more quality indices that is higher than remaining channels in each channel.

In some embodiments, the applying the deep learning architecture may include encoding each tensor for each window of the one or more periods using the deep convolutional network into one or more deep learning features associated with cardiac activity. The applying may also include applying the bidirectional recurrent network to determine a probability that each window of the one or more periods belongs to a class of the one or more classes. The bidirectional recurrent network may use the one or more deep learning features, the one more signal quality indices for the cardiac data and/or motion data, and/or one or more cardiovascular features to classify each window of the one or more periods. The applying may also include determining the classification of cardiac activity for each window of the one or more periods and/or each period by applying the attention network to the probability for each window of the one or more periods.

In some embodiments, the attention network may determine a score for each window and/or each period, the score representing the classification of cardiac activity. In some embodiments, when the classification of cardiac activity includes abnormal cardiac activity, a window of each period having a highest score may represent the window including the abnormal cardiac activity.

In some embodiments, the systems may include a system for using machine learning to determine abnormal cardiac activity of a subject. The system may include a memory; and one or more processors. In some embodiments, the one or more processors may be configured to cause receiving one or more periods of time of cardiac data and motion data for a subject. Each period of time including more than one window of the cardiac data and the motion data. The one or more processors may further be configured to cause determining one or more signal quality indices for each window of the cardiac data and the motion data of the one or more periods of time. The one or more processors may also be configured to cause extracting one or more cardiovascular features for each period of time using at least the cardiac data, the motion data, and the one or more signal quality indices for the cardiac data and the motion data. The one or more processors may be configured to cause applying a tensor transform to the cardiac data and/or the motion data to generate a tensor for each window of the one or more periods of time. The one or more processors may be configured to cause applying a trained deep learning architecture to each tensor of the one or more periods of time to classify each window and/or each period into one or more classes using at least the one or more signal quality indices for the cardiac data and the motion data and cardiovascular features. In some embodiments, the deep learning architecture may include a convolutional neural network, a bidirectional recurrent neural network, and an attention network. The one or more classes may include abnormal cardiac activity and normal cardiac activity. The one or more processors may be configured to cause generating a report including a classification of cardiac activity of the subject for the one or more periods based on the one or more classes.

In some embodiments, the one or more processors may be further configured to cause receiving subject contextual information for the subject. The subject contextual information may include medical history and demographic information. The extracting may use one or more subject information features related to the subject contextual information to extract one or more cardiovascular features for each period of time, and the trained deep learning architecture may use the one or more subject information features to classify the cardiac activity for each window of the period.

In some embodiments, the tensor transform may be applied to the cardiac data and the motion data for each window.

In some embodiments, the one or more processors may be configured to cause determining a quality channel for each window based on the one or more signal quality indices for the cardiac data and the motion data. The quality channel may correspond to a channel in each window having the one more quality indices that is higher than remaining channels in each channel.

In some embodiments, the applying the deep learning architecture may include encoding each tensor for each window of the one or more periods using the deep convolutional network into one or more deep learning features associated with cardiac activity. The applying may also include applying the bidirectional recurrent network to determine a probability that each window of the one or more periods belongs to a class of the one or more classes. The bidirectional recurrent network may use the one or more deep learning features, the one more signal quality indices for the cardiac data and/or motion data, and/or one or more cardiovascular features to classify each window of the one or more periods. The applying may also include determining the classification of cardiac activity for each window of the one or more periods and/or each period by applying the attention network to the probability for each window of the one or more periods.

In some embodiments, the attention network may determine a score for each window and/or each period, the score representing the classification of cardiac activity. In some embodiments, when the classification of cardiac activity includes abnormal cardiac activity, a window of each period having a highest score may represent the window including the abnormal cardiac activity.

In some embodiments, the cardiac data may include ECG and/or PPG data. In some embodiments, the motion data may include accelerometer data.

In some embodiments, the cardiac data and/or the motion data may be received from one or more sensor data collections device including one or more cardiac sensors configured to detect cardiac data and one or more motion sensors configured to detect motion data. In some embodiments, the one or more sensor data collection devices includes a wearable device, such as a smart watch.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure can accurately determine abnormal cardiac activity a subject (e.g., a human subject, a patient, an animal, (e.g., equine, canine, porcine, bovine, etc.), etc.). The systems and methods of the disclosure use more than one neural network to determine abnormal cardiac activity based on cardiac and motion data, such as ECG or PPG data and accelerometer data. This can result in improved performance compared to cardiac data (e.g., PPG or ECG) based approaches that rely only on beat detection.

As used herein, "cardiac activity" may relate to the function of the heart for a period of time. In some embodiments, the cardiac activity may relate to normal cardiac activity (normal sinus rhythm) or abnormal cardiac activity. Abnormal cardiac activity may relate to any cardiac abnormality that can be identifiable on cardiac and/or motion data. The abnormal cardiac activity may be arrhythmic and/or non-arrhythmic. By way of example, an arrhythmia refers to a cardiac arrhythmia, (also known as cardiac dysrhythmia), which can refer to an irregular timing or morphology in a heart beat or sequence of beats. For example, abnormal cardiac activity may include but is not limited to arrhythmias, such as atrial fibrillation, ventricular tachycardia, sinus tachycardia, sinus bradycardia, atrial flutter, atrial tachycardia, junctional tachycardia, premature ventricular complex, premature atrial complex, ventricular premature contraction, among others; other abnormal cardiac activity, such as acute myocardial infarction, myocardial infarction, ischemia, among others; or any combination thereof. Although the application is described with respect to atrial fibrillation, the methods and systems can be configured to detect additional and/or other abnormal cardiac activity (e.g., arrhythmias).

Figure 1:
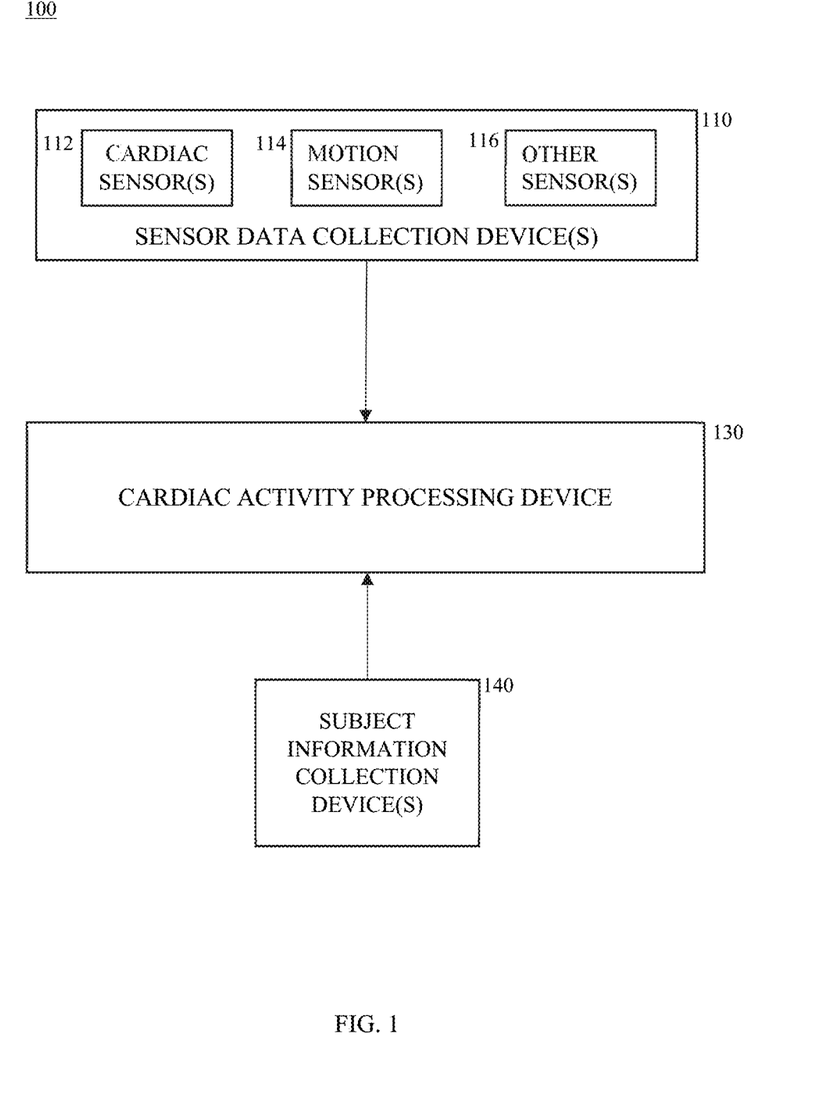
FIG. 1 shows an example of a system that can be used to determine cardiac activity according to embodiments.

FIG. 1 shows a system 100 that can determine cardiac activity using cardiac and motion data according to embodiments. In some embodiments, the system 100 may include one or more sensor collection devices 110 configured to collect at least the motion data and the cardiac data, and a cardiac activity processing device 130 configured to determine cardiac activity using at least the motion data and the cardiac data. In some embodiments, the one or more sensor collection devices 110 may include one or more cardiac sensors 112 and one or more motion sensors 114.

In some embodiments, the cardiac data may relate to a signal related to a function of a subject's heart. By way of example, the cardiac data may include but is not limited to PPG data, ECG data, electromyographic data, electroencephalographic data, phonocardiographic (PCG) data, ballistocardiographic data, blood pressure data, among others, or any combination thereof. The one or more cardiac sensors 112 may include but are not limited to PPG sensor(s), ECG sensor(s), electromyographic sensor(s), electroencephalographic sensor(s), phonocardiographic (PCG) sensor(s), acoustic sensor(s), optical sensor(s), ballistocardiographic sensor(s), video or camera sensor(s), off-body sensor(s) (e.g., radar sensor(s), video or camera sensors (s)), among others, or a combination thereof. By way of example, the one or more sensors electrocardiograph (ECG) sensors may include direct contact electrodes on the skin or capacitive contact; opto-electrical photoplethysmography (PPG) measurements may include light source, e.g., a light emitting diode (LED) and photodetector (e.g. transistor/diode or a photodiode (PD)) as a receiver against the skin, LED and Photo diode arrays as transmitter-receiver pairs against the skin, a camera as a detector; a PCG sensors may include a Giant-Magneto-Resistance (GMR) sensors; acoustic sensors may include an acoustic sensor based microphone; and off-body sensors may include off-body devices such as radar, cameras, LIDAR, etc.

In some embodiments, the motion data may relate to body motion of the subject. In some embodiments, the one or more motion sensors 114 may include but are not limited to an accelerometer, gyroscope, among others, or a combination thereof. By way of example, the accelerometer may be configured to detect accelerations of body parts of the subject and be configured to detect motion (e.g., posture changes) of the subject by determining changes in average orientation of the accelerometer with respect to gravity.

In some embodiments, the cardiac sensor(s) 112 and the motion sensor(s) 114 may be embedded within or otherwise coupled to (or interoperate with) one or more sensor collection devices 110 that can be removably attached to a user. By way of example, one sensor collection device may be a wearable device, such as a smart watch, glasses, a headband, helmet, a smart phone attached using an attachment device (e.g., arm band).

In some embodiments, the cardiac sensor(s) 110 and the motion sensor(s) 120 may be embedded within or otherwise coupled to one sensor collection device 110. For example, the one sensor collection device 110 may be a smart watch including at least the cardiac and motion sensors that can be attached to an individual's wrist, for example, using a wrist band.

In some embodiments, each of the cardiac sensor(s) 110 and the motion sensor(s) 120 may be disposed within or otherwise coupled to a sensor collection device 110 so that they are each disposed on their respective sensor collection device. By way of example, the one or more sensor collection devices 110, for example, for the cardiac sensor(s) 110, can be removably attached to an individual using a patch (e.g., adhesive patch, sticker, etc.)

In some embodiments, the one or more sensor data collection devices 110 may also include one or more other sensors 116. In some embodiments, the one or more other sensors 116 may include but are not limited to a thermometer, location (such as GPS), galvanic skin response/electrodermal activity sensors, among others, or a combination thereof.

In some embodiments, the system 100 may further include one or more subject information collection devices 140. The subject information collection device(s) 140 may include one or more devices or systems or otherwise be configured to communicate with systems or devices that are configured to collect and/or store the subject information. By way of example, the subject information (also referred to as "subject contextual information") may include contextual information about the subject, such as medical history information (e.g., history of heart disease, current and past medication history (e.g., medication, dosages, etc.), treatment history, devices, weight, height, etc.), demographic information (e.g., age, gender, etc.), activity information, other contextual information/covariates, or any combination thereof. For example, the subject information collection device(s) 140 may be configured to communicate with one or more electronic medical record (EMR) systems that store health and/or demographic information of the subject to retrieve the medical history information. In another example, the subject information may be provided by the subject and/or another user (e.g., clinician) using an interface. For example, the subject or clinician may provide the information using a mobile or computer application. In some embodiments, the subject information may be collected by questionnaires on psychosocial activity (e.g. PHQ9), preexisting prior information, such as the NYHA classification. In some embodiments, the subject information collection device 140 may be configured to communicate with one or more applications to retrieve subject contextual information (e.g., such as fitness application(s)) to retrieve information related to fitness or physical activity).

In some embodiments, the cardiac activity determination device 130 may be configured to determine cardiac activity based on at least the motion data and the cardiac data (and optionally the subject information) using a deep learning architecture. In some embodiments, the deep learning architecture may include more one or more (trained) deep neural networks. In some embodiments, the one or more trained deep neural networks may include a convolutional neural network, a bidirectional recurrent neural network, an attention network, among others, or a combination thereof. The one or more deep learning networks may be trained based on training samples of motion data and/or cardiac data having known cardiac activity features, such as known abnormal cardiac activity, known subject information (e.g., medical and/or demographic information (e.g., age, medication use, device use, etc.)), among others, or combination thereof.

The cardiac activity determination device 130 may be configured for multi-class classification of cardiac activity using at least the motion data and the cardiac data. For example, the cardiac activity determination device 130 may be configured to determine whether the cardiac activity for a period of time corresponds to the one of the following classes: normal, noise, abnormal, among others, or combination thereof. In some embodiments, abnormal class may any abnormal cardiac activity. In some embodiments, the abnormal class may refer to one type of abnormal activity (e.g., atrial fibrillation). In some embodiments, the abnormal class may refer to more than one type of abnormal activity (one or more arrhythmic abnormalities and/or non-arrhythmic abnormalities).

In some embodiments, the cardiac activity determination device 130 may be embedded in or interoperate with various computing devices, such as a mobile phone, a cellular phone, a smart phone, a personal computer (PC), a laptop, a notebook, a netbook, a tablet personal computer (tablet), a wearable computer (e.g., smart watch, glasses etc.), among others, or a combination thereof.

In some embodiments, the one or more sensor data collection devices 110, the cardiac activity processing device 130, and/or the subject information collection device 140 may be disposed within the same device or otherwise have connectivity via a communication network. By way of example, the communication network of system 100 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Although the systems/devices of the system 100 are shown as being directly connected, the systems/devices may be indirectly connected to one or more of the other systems/devices of the system 100. In some embodiments, a system/device may be only directly connected to one or more of the other systems/devices of the system 100.

It is also to be understood that the system 100 may omit any of the devices illustrated and/or may include additional systems and/or devices not shown. It is also to be understood that more than one device and/or system may be part of the system 100 although one of each device and/or system is illustrated in the system 100. It is further to be understood that each of the plurality of devices and/or systems may be different or may be the same. For example, one or more of the devices of the devices may be hosted at any of the other devices.

Figure 8:
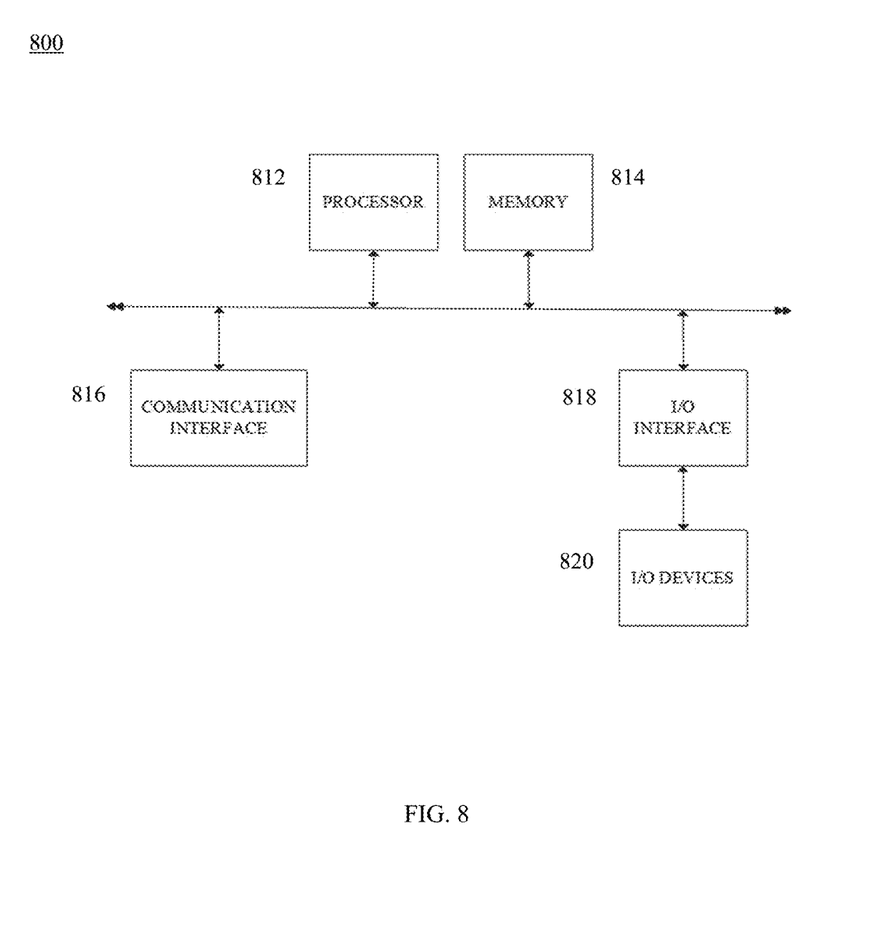
FIG. 8 shows a block diagram illustrating an example of a computing system.

In some embodiments, any of the devices of the system 100, for example, the cardiac activity processing device 130, may include a non-transitory computer-readable medium storing program instructions thereon that is operable on a user device. A user device may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, wearable computer (e.g., smart watch), or any combination thereof, including the accessories and peripherals of these devices, or any combination thereof. FIG. 8 shows an example of a user device.

Figure 2:
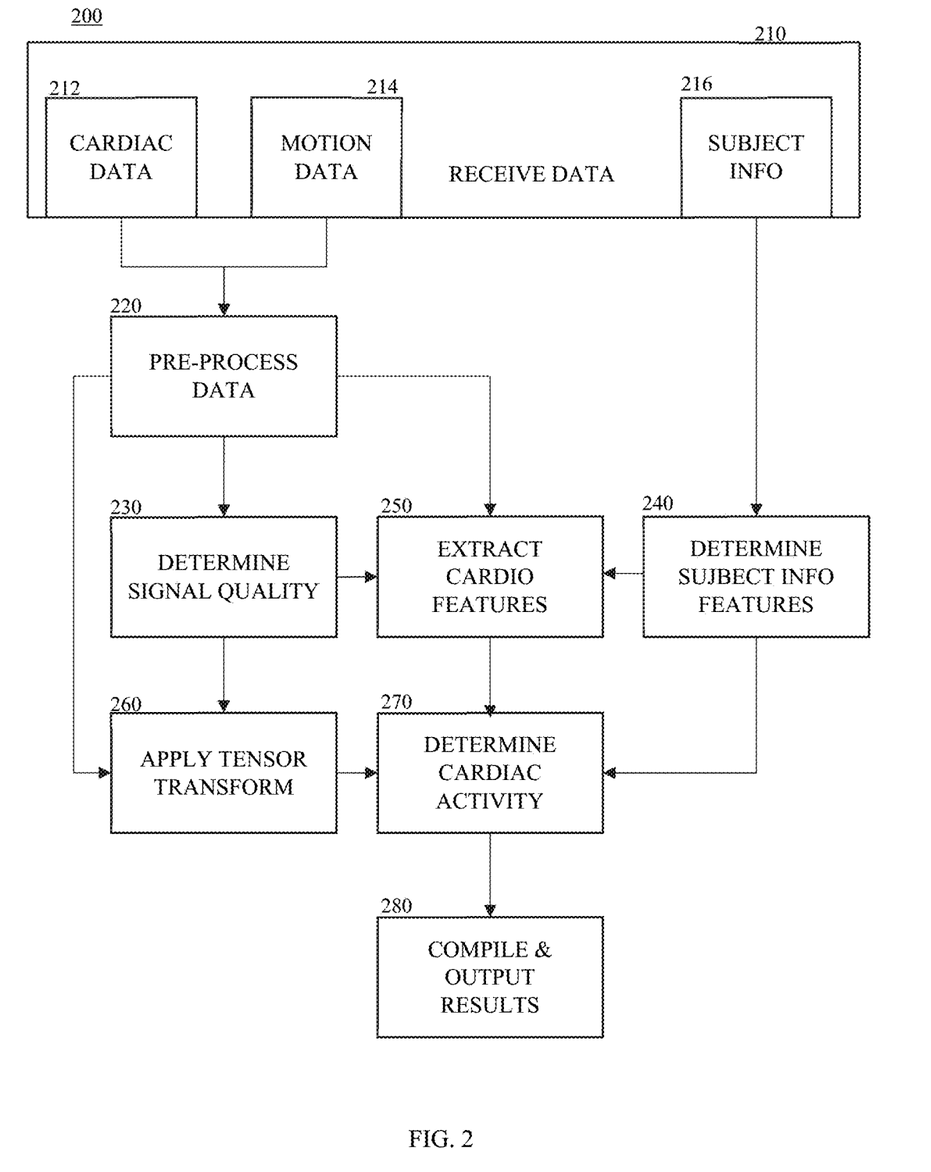
FIG. 2 shows a method of determining cardiac activity according to embodiments.
Figure 3:
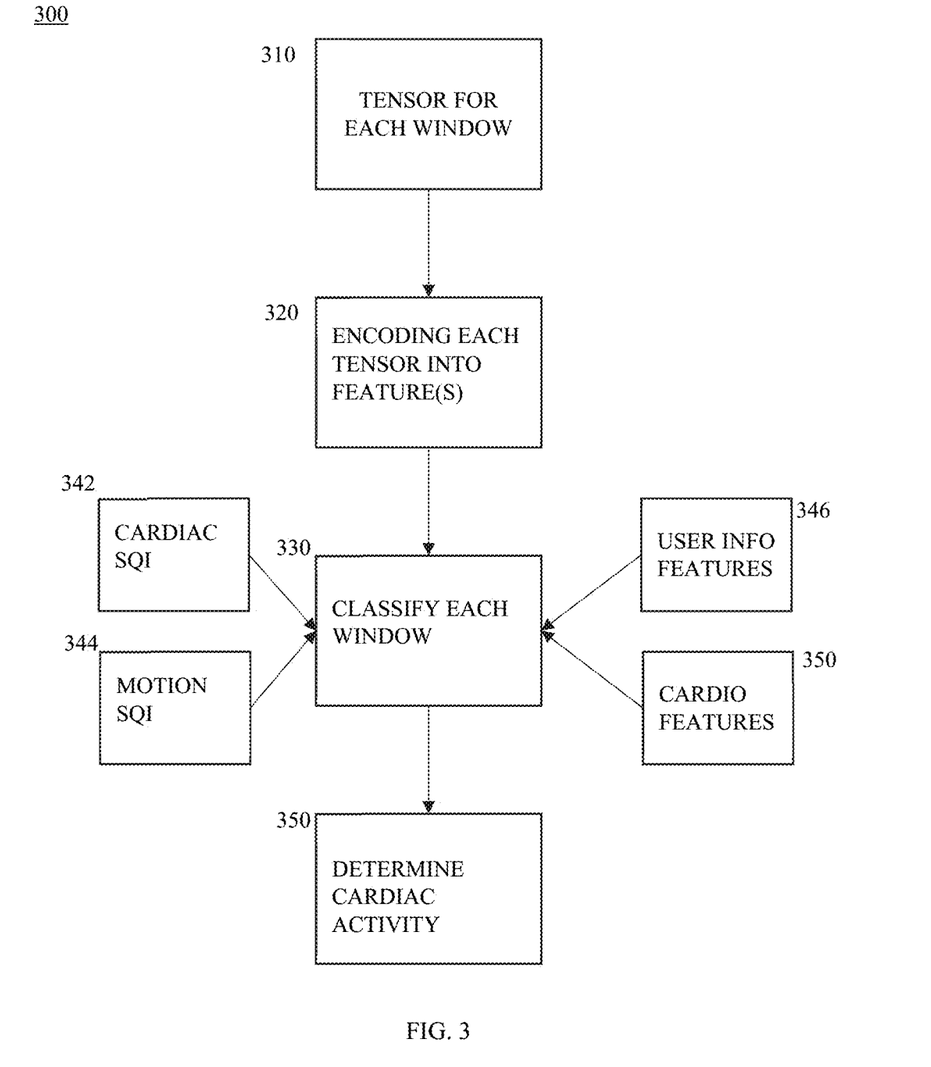
FIG. 3 shows a method of classifying the cardiac activity according to embodiments.

FIGS. 2 and 3 show methods of determining abnormal cardiac activity according to embodiments. Unless stated otherwise as apparent from the following discussion, it will be appreciated that terms such as "encoding," "generating," "determining," "displaying," "obtaining," "applying," "processing," "computing," "selecting," "receiving," "detecting," "classifying," "calculating," "quantifying," "outputting," "acquiring," "analyzing," "retrieving," "inputting," "assessing," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 8. Other systems may also be used.

The methods of the disclosure are not limited to the steps described herein. The steps may be individually modified or omitted, as well as additional steps may be added. It will be also understood that at least some of the steps may be performed in parallel.

FIG. 2 illustrates a method 200 for determining cardiac activity based on at least motion and cardiac data. For example, the method 200 may result in a diagnosis of abnormal cardiac activity (e.g., atrial fibrillation) or a burden thereof.

In some embodiments, the method 200 may include a step 210 of receiving the data for the subject. In some embodiments, the step 210 may include receiving the cardiac data 212 and the motion data 214 from the one or more sensors (e.g., sensor(s) 112 and sensor(s) 114, respectively, for the one or more period of times (referred to also as "time period") via the sensor collection device(s) 110.

In some embodiments, the step 210 may optionally include receiving the subject information 216, for example, from the subject information collection device(s) 140. In some embodiments, for example, if multiple periods of cardiac and motion data are processed for the subject, the system 100 may store the subject information (e.g., the features determined step 240) received from the subject information collection device(s) 140.

In some embodiments, the method 200 may include a step 220 of pre-processing the motion data and the cardiac data for each period of time to prepare the data for classification.

In some embodiments, the pre-processing 220 may include dividing each time period of the motion and cardiac data into a plurality of non-overlapping windows of time. In some embodiments, the windows may be of any interval. For example, each window of data may be thirty seconds, less than thirty seconds (e.g., 20 seconds), more than thirty seconds (e.g., 1 minute, 2 minutes), etc. In some embodiments, each window may be of the same size.

In some embodiments, the cardiac activity processing device 130 may receive a set of motion and cardiac data for a length of time (e.g., an hour period) and may divide the set into a plurality of time periods for processing. For example, the step 220 may include separating the hour of motion and cardiac data into ten-minute periods and may include further separate each ten-minute period into thirty second windows.

In some embodiments, the pre-processing step 220 may also include processing the motion and cardiac data each window and/or period to remove any noise or outlier. For example, for the cardiac data and/or motion data, the step 220 may include applying a threshold or a filter (e.g., bandpass filter) to the cardiac data and/or motion data to remove any outlier data and setting the outlier data to a set value, for example, the corresponding threshold. In some embodiments, for cardiac data, the step 220 may also include amplitude normalization for each non-overlapping window of data, sphering to adjust for inter-device offsets, and bandpass filtering and resampling with an anti-alias filter.

In some embodiments, the step 220 may also include determining pulse onset detection for each window. For example, the pulse onset detection may be determined using a gradient slope thresholding technique, zero crossing of an envelope function, an autocorrelation estimation process, or a model-based fitting process.

By way of example, for PPG data, for each normalization second window segment of each PPG color channel, outlier rejection and amplitude normalization may be performed. For example, the lower 5-percentile and upper 95-percentile of the PPG signal within each window segment may be calculated after subtracting the signal mean. The lower and upper percentile may correspond to the thresholds and any signal value surpassing these two thresholds can be set to the corresponding threshold (e.g., extreme value clipping). After which, each window may be normalized by the maximum value in the segment. Next, each PPG channel can be bandpass filtered to remove frequencies outside a normal range (e.g., range of 0.2-10 Hz, using an FIR filter of order 41). Within each window, PPG pulse onset detection (e.g., using the slope sum function (SSF) approach) can be determined.

In some embodiments, the method 200 may include a step 230 of determining a signal quality associated with each window of the cardiac data and the motion data of each time period. In some embodiments, the signal quality may be represented by one or more signal quality indices(s) (SQI). The step 230 may include determining one or more signal quality indices for the cardiac data and the motion data. For example, the signal quality may be determined by using a template matching process.

In some embodiments, the signal quality of the cardiac data may be analyzed using two different detectors (heart beat or peak/slope). By way of example, the signal quality data index for the cardiac data may relate to a proportion of disagreements in the detectors.

For example, for the cardiac data, a signal quality index may be determined for each window using two different beat detectors. One detector may be highly sensitive and one may be highly specific. By way of example, the signal quality index for the cardiac data may be determined using the Hjorth's purity quality metric. The signal quality index may be a percentage of beats that are agreed upon by two beat detectors with different noise responses. By way of example, for PPG and/or ECG data, a signal quality index may be determined for each channel in each window.

In some embodiments, the motion data may include one or more signal quality indices related to energy. In some embodiments, a signal quality index for motion data (may be determined using the average value of the magnitude of the accelerometer for each window. By way of example, for accelerometer data, the first signal quality index may be determined using the average value of the magnitude of the accelerometer data ($ACC=\sqrt{x^2+y^2+z^2}$) within each window. In some embodiments, an alternative or additional quality index for the motion data may be determined using the standard deviation of the motion data within each window. By determining the SQI for the motion data, large movements that can cause low quality data can be identified.

In some embodiments, the signal quality index for each of the cardiac and motion data may be combined (e.g., Boolean sense) or may remain separate variables, or a combination thereof.

In some embodiments, the step 230 may also include determining a quality channel for each window of cardiac data based on one or more signal quality indices determined for each channel in the respective window. The quality channel may correspond to the channel with the highest signal quality (e.g., having the high signal index or indices) and the data (i.e., features) from this channel can be selected to represent the corresponding window.

In some embodiments, the step 230 may include determining a quality window for the motion data. The quality window may correspond to the window having the lowest amount of energy (e.g., is lowest acceleration energy window). In some embodiments, the step 230 may include determining a quality window for each period using the SQI for the cardiac and motion data. The quality window for each period may correspond to the window with the highest signal quality and least ACC.

In some embodiments, the method 200 may optionally include a step 240 of determining one or more subject information features (also referred to as "subject contextual information features") for example, from the subject information collected by the subject information device 140. The subject information features may relate to any relevant contextual information, such as medical history and/or demographics. For example, the medical history information and/or demographic information may be processed to determine or identify the history of certain medications (e.g., beta-blockers, calcium blockers, blood thinners), dosage of medications, device usage (e.g., pacemaker), history of certain medical events (e.g., stroke, myocardial infraction, etc.), age, gender, weight, among others, or a combination thereof. Such information can modify the interpretation of features at various stages of processing. In some embodiments, the subject information features may be stored by the system 100 after an initial determination for the subject for processing the set(s) of cardiac and motion data received for the patient.

In some embodiments, the method 200 may include a step 250 of extracting one or more cardiovascular features using the (raw and/or pre-processed) cardiac data, the (raw and/or pre-processed) motion data, one or more SQI (e.g., cardiac and/or motion SQI), the subject information (features), among others, or any combination thereof. By way of example, one or more cardiovascular features may be based on beat-to-beat-interval variations. For example, the one or more cardiovascular features may include but are not limited to one or more entropy or cross-entropy related features, one or more standard deviation features, among others, or any combination thereof. The features may be determined for each channel, all channels, between cahllens (cross information) or a combination thereof.

By way of example, for PPG and/or ECG data, one or more cardiovascular features for each window may be determined using the cardiac data for one channel, such as the quality channel determined for that window By way of example, a first sample entropy feature for the cardiac data may be determined for each window with the embedding dimensions m=1, and 2. For example, a first standard deviation feature for the cardiac data may be determined by determining a standard deviation of all channels of all windows of the period using the raw cardiac data for the period of time. A second standard deviation feature, which is a more robust version of the standard deviation may also be determined for all channels of all windows using the pre-processed cardiac data, because it discards the intervals outside the 0.05-0.95 percentile range.

For example, a third weighted standard deviation feature may be determined for the motion data. By way of example, for accelerometer data, the inverse of the ACC waveform within each window may be used as the weighing factor for when calculating the standard deviation.

In some embodiments, the method 200 may include a step 260 of applying a tensor transform applying a tensor transformation to the cardiac data and/or motion data for each window to transform the data to time-frequency space. The tensor transformation may include but is not limited to wavelet transform, short-time Fourier transform (STFT), a Gabor transform, a compressed matrix, among others, or a combination thereof. In some embodiments, the tensor transform may be performed on the cardiac data associated with the highest quality channel for each window. The tensor transform may result in a tensor for each window. In some embodiments, the tensor transformation may be applied to the raw cardiac data and/or motion data associated with each window and/or channel.

In some embodiments, the tensor transform may be a uni-modal tensor transformation (such as wavelet transform of the cardiac data) or a multi-modal tensor transformation (such a cross-wavelet transform of motion and cardiac data). For example, the motion data may include respiratory activity (which can depend on the location of the motion sensor) and the resulting cardio-respiratory cross-wavelet transform (or other transform) can represents the cross-frequency coupling. Such information can be useful for arrhythmia detection as it can enable the classifier (step 270) to distinguish between respiratory induced variability in rhythm versus arrhythmia related rhythm irregularity.

In some embodiments, the tensor transformation may be a wavelet transformation. For example, the size of the wavelet spectrum computed may be sized 125×125 and the mother wavelet may be the "Morlet wavelet." After which, the derived wavelet power spectrum may be further processed to remove the contribution of noise to the spectrum, for example, by normalizing each window using the maximum wavelet power determined for the period of cardiac data and/or motion data (i.e., all windows for that period) (depending on whether the transformation is uni-modal or multi-modal). By way of example, the statistical significance level of the wavelet power may be estimated, for example, using a Monte Carlo method. Next, a large ensemble of surrogate data (N=100) may be generated with the same first order autoregressive (R1) coefficients as the input signals. For each surrogate data, a wavelet power for each window may be calculated and thresholded using a maximum wavelet power (e.g., using the 95-percentile of the power as the threshold above which the observed signal power can be considered statistically significant (at 5% significance level)). The resulting wavelet power spectrum for each window (the wavelet power above the threshold) corresponds to the resulting tensor corresponding to the window. Each tensor may correspond to a window of cardiac data or a window of cardiac and motion data combined.

Figure 4:
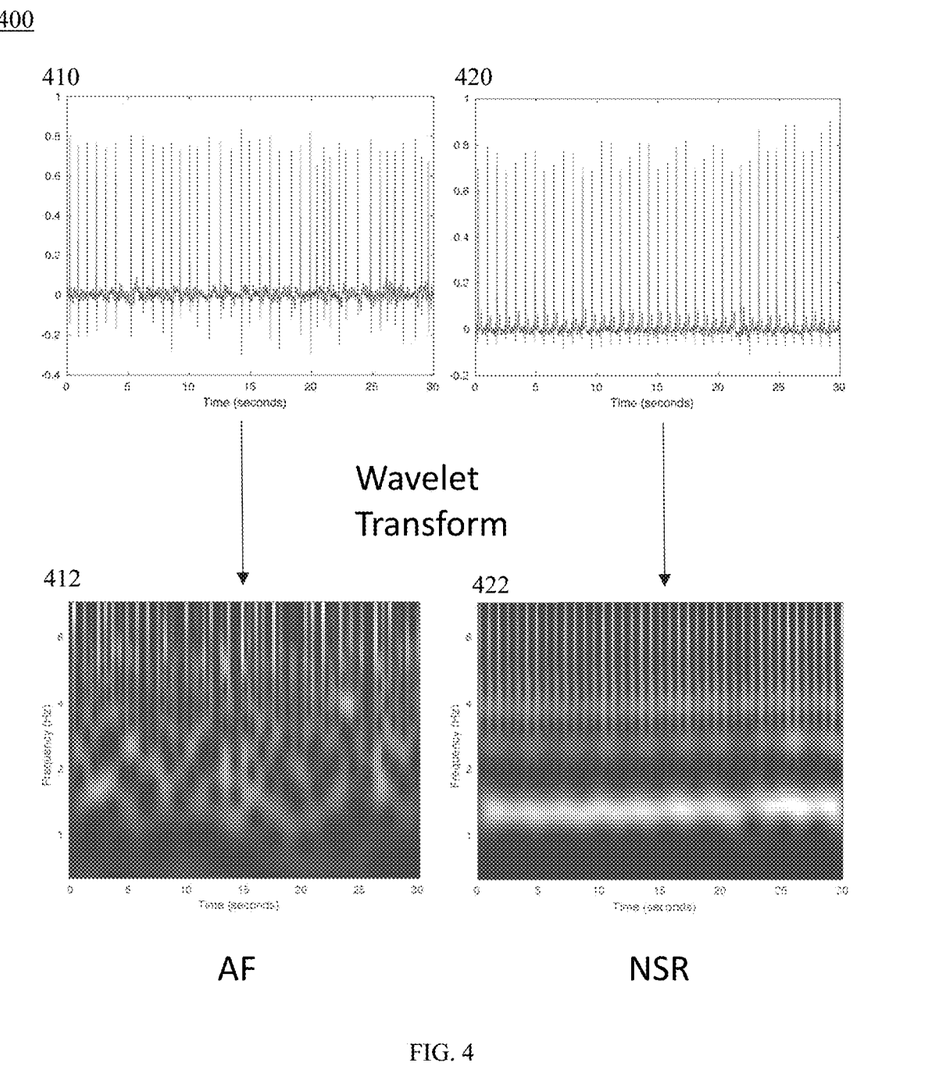
FIG. 4 shows an example of a tensor transformation according to embodiments.

By way of example, FIG. 4 shows an example of a wavelet transformation being performed on a window 410 of cardiac data and a window 420 of cardiac data. As shown in FIG. 4, the transformation results in tensors 412 and 422 in which the cardiac data may be mapped into a larger representation that emphasizes the differences in patterns between abnormal cardiac activity (i.e., atrial fibrillation) and other classes (i.e., normal cardiac activity (normal sinus rhythm) or noise), respectively.

In some embodiments, the method 200 may include a step 270 of determining cardiac activity using one or more neural networks based on cardiac SQI (step 230), motion SQI (step 230), user information features (step 240), cardiovascular features (step 250), or any combination thereof. For example, the step 270 may determine whether the subject had an occurrence of abnormal cardiac activity (e.g., atrial fibrillation) at a time point within the time period and the time point associated with each occurrence of abnormal cardiac activity.

In some embodiments, the step 270 may include processing the tensor for each window (step 260) using one or more neural networks to determine cardiac activity associated with each window. The one or more neural networks may include neural networks that differ from each other in at least one of architecture and/or functionality (e.g., convolutional neural networks, recurrent neural networks), feature input and/or type (e.g., cardiac, motion, user information features), among others, or a combination thereof. In some embodiments, the cardiac activity may be determined using an attention network (mechanism) that is connected in series to other neural network(s).

In some embodiments, the one more neural networks may include a convolutional neural network that extracts deep learning features from the tensor for each window (e.g., as a feature vector) and a bidirectional recurrent neural network (RNN) that maps the deep learning features, cardiac and/or motion SQI indices, and user information, to a class probability. In some embodiments, the one or more neural networks may also include an attention network. The attention network may determine the optimal sections of data to analyze to provide a weight for each window of a time period. The attention network may use the weighted combinations of windows to determine a classification of the subject. The classification using the attention network may result in a diagnosis of abnormal cardiac activity, type of abnormal cardiac activity, and/or burden of the abnormal cardiac activity (i.e., percentage of time that a patient exhibits abnormal cardiac activity (total time in abnormal cardiac activity (e.g., AF) divided by the period of time)). Using the weights from the attention model, the window in which the abnormal cardiac activity (e.g., arrhythmia) occurs may be identified. For example, the window with the highest weight may be considered the window in which the abnormal cardiac activity occurred. This can be provided to the clinician in a report.

The one or more neural networks may be a trained multi-class classifier. In some embodiments, the deep convolutional network may be trained by processing on a set of tensors to learn one or more deep learning features associated with abnormal and normal cardiac activity.

In some embodiments, the resulting networks (CNN, RNN and attention network) may then trained together (end-to-end), for example, training the attention network and RNN using the learning features extracted by the CNN, so as to optimize the classifier.

In some embodiments, the method 200 may include a step 280 of compiling and outputting the results of the determination of cardiac activity for one or more periods of time. For example, the results (step 270) may be transmitted (e.g., to the clinician), printed, displayed, stored, among others, or any combination thereof. In some embodiments, the results may be outputted as a report. In some embodiments, the report may include the results of the determination for one or more periods of time (step 270). For example, the results of the determination of cardiac activity (step 270) may include a diagnosis of abnormal or normal cardiac activity, type of abnormal cardiac activity, and/or a burden of cardiac activity; one or more windows including abnormal cardiac activity with the abnormal cardiac activity identified; among others, or combination thereof.

In some embodiments, the report may compile the results of the analysis and classification for more than one period of time. For example, as previously noted, the system 100 may receive a set of cardiac and motion data for a length of time (e.g., 1 hour) and may separate that into a plurality of periods of time (e.g., six periods of time). In this example, the system 100 may repeat steps 220-270 for each period of time and compile the results for the length of time in the output (e.g., report) (step 280). In this example, if abnormal cardiac activity is determined in more than one period (e.g., at least one window in one period is determined to include abnormal cardiac activity), the burden may be determined using all periods of time.

FIG. 3 shows an example of a method 300 of determining cardiac activity using the tensor 310 for each window (from step 260), based on SQI for cardiac data (from step 230), SQI for motion data (step 230), one or more cardiovascular features (step 250), and/or user information features (from step 240) for each period of time according to some embodiments.

In some embodiments, the method 300 may include a step 320 of encoding each tensor 310 for each window of the period (from step 260) into one or more deep learning features (e.g., feature vectors) associated with cardiac activity (e.g., abnormal and normal cardiac activity) using the deep convolutional network (CNN) according to embodiments.

By way of example, the CNN can extract deep learning features from each tensor, which is in a 2 dimensional space, and project it to a smaller 1 dimensional feature vector. In some embodiments, the CNN may include one or more convolutional and max-pool layers. In some embodiments, the CNN may include ten or more convolutional and fully connected layers. Nodes may be automatically pruned, and optimized to act as filters to create feature vectors (i.e., deep learning features) from the input tensor in each window.

Figure 5:
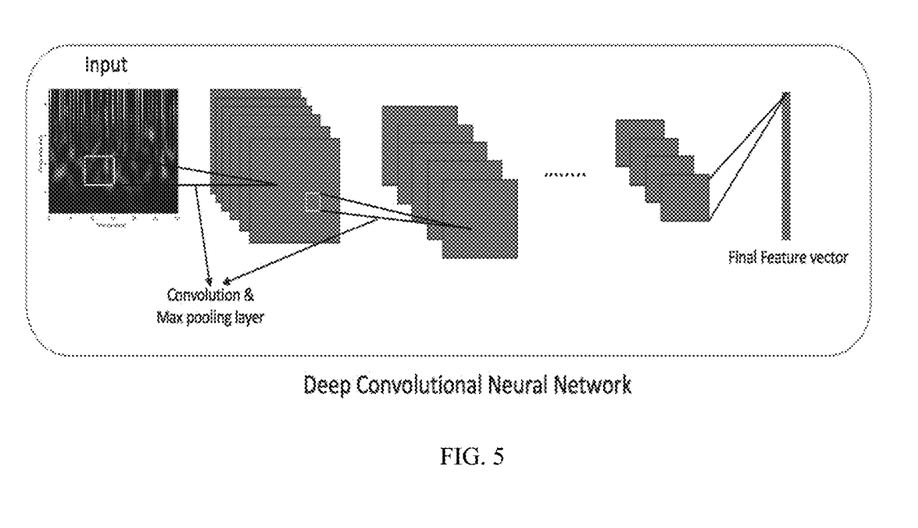
FIG. 5 shows an example of deep convolutional neural network according to embodiments.

FIG. 5 shows an example 500 of a method of encoding of regions of each tensor for each window into one or more deep learning features (e.g., feature vectors) using the deep convolutional network according to some embodiments.

In some embodiments, the method 300 may further include a step 330 of classifying each window of cardiac data and/or motion data into one more classes of each period of time using the deep learning features (vectors) representing each window (step 320); the signal quality indices 342 and/or 346 for the respective window (from step 230), one or more subject information features 346 (step 240), and/or one or more of the cardiovascular features 348 (step 250). In some embodiments, the classifying 330 of each window of the period may be performed by a bidirectional recurrent neural network. In some embodiments, the classifying 330 may determine a probability that each window belongs to a class of one or more classes. The classes may include but are not limited to abnormal cardiac activity (e.g., type, presence, etc.), normal cardiac activity, noise, among others, or a combination thereof.

Figure 6:
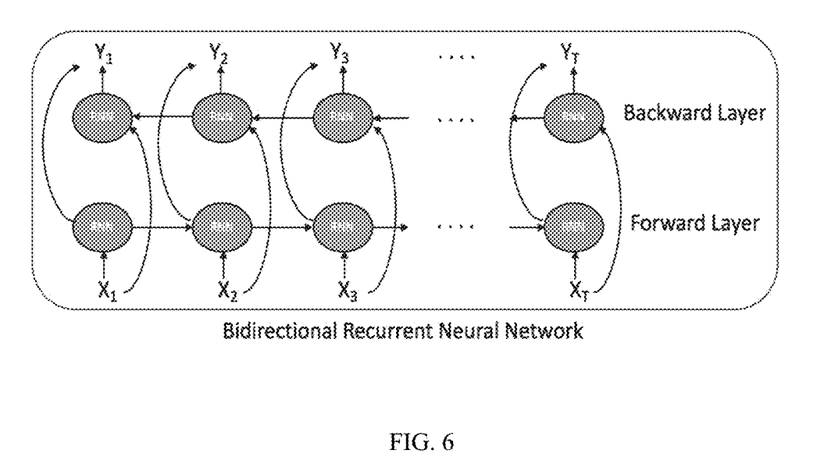
FIG. 6 shows an example of a bidirectional recurrent neural network according to embodiments.

In some embodiments, the bidirectional recurrent neural network may include stacking multiple layers to predict the probability (or weight) of each deep learning feature for each window belonging to a class, with the output sequence of one layer forming the input sequence for the next. FIG. 6 shows an example of a bidirectional recurrent neural network that encodes the CNN feature vector, in addition to the cardiovascular features, SQI, and/or subject information features, to account for temporal characteristics of the signal. As shown in this figure, the input, X, which represents the CNN feature vector, in addition to the cardiovascular features, SQI, and/or subject information features, for each window (1, 2, ... T), can be fed into a bidirectional RNN.

The forward and backward passes can allow the neural network to express an opinion (i.e., a weight) regarding cardiac activity (e.g., abnormal cardiac activity) at each time-step (each window), by analyzing the set of inputs for the current window (e.g., i), and (1) the previous window (e.g., i−1) and (2) the following window (i+1). For example, for the forward pass, the input (X) for each window (i)(e.g., (1, 2, ... T)) can be inputted into the forward layer, which are used to update the hidden units of the RNN. The backward pass may include updating the hidden units and outputting a class probability vector ($Y_i$) for each window (i=1,2, ... ,T) in the reverse direction for further analysis (e.g., using the outputs from the previous window and following window). After the forward pass of all inputs ($X_i$, i=1, 2, ... , T) for the period and update of the hidden units, the backward pass can ensure that the hidden units include information from both proceeding and succeeding windows (also referred to as the "smoothed hidden units"). The smoothed hidden units can then be used to update the corresponding outputs ($Y_i$, i=1,2, ... ,T), which can then be inputted into the attention network.

In some embodiments, the method 300 may further include a step 350 of determining cardiac activity associated with each window of each period of time based on the classification from step 330.

In some embodiments, the step 350 may include inputting the output ($Y_i$, i=1,2, ... , T) from step 330 (i.e., from RNN) into an attention network to determine a diagnosis related to abnormal cardiac activity (e.g., incidence of atrial fibrillation) or burden of abnormal cardiac activity. In some embodiments, the attention network may provide a score as an output for each window. The score may correspond to a weighted combination of the weights (or probabilities) determined for each window (step 330). In some embodiments, the score may be indicative of the class (e.g., abnormal, normal, noisy, other, etc.).

In some embodiments, the attention network can determine the optimal sections of data to analyze, or how to relatively weigh combinations of windows to provide a final diagnosis or burden. It can also identify the time(s) at which the cardiac activity occurred. This way, the clinician may review the results of the systems and devices of the disclosure.

Figure 7:
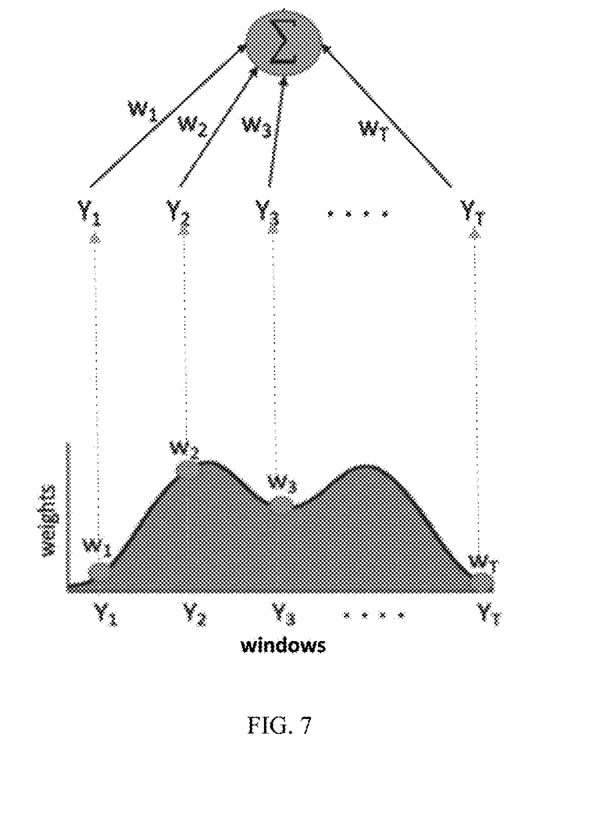
FIG. 7 shows an example of an attention network according to embodiments.

For example, FIG. 7 shows an example of an attention network according to embodiments. In this example, the final output, $Y_{attention}$, corresponding to the classification of the cardiac activity of a subject for a period of time, can be formed by taking all of the Y(RNN outputs) for each window (i), $Y_i$, and weighting them by the degree of importance each window of cardiac data should have in the period of time. The outputs ($Y_i$, i=1,2, ... ,T) from the RNN (step 350) may then be weighted by the corresponding attention model weights ($w_i$), to produce the final outputs for each period. The final outputs ($Y_{attention}$) for each window of each period corresponds to $Y_{attention} \Sigma_{i=1}^{T} w_i Y_i$. The weight for each window can be based on criteria, including but not limited to: cardiac SQI, motion SQI, tensor(s), probability (output from step 330), health information, among others, or a combination thereof. This weighting, or "attention" can determined by optimization of the weights over the entire training set, using back propagation. The score may correspond to a sum of each weight determined for the window.

In some embodiments, the window having the highest weight (or score) in each period may be considered the window time having an abnormality.

By way of example, for a multi-class classification of subject data with classes: normal cardiac activity, Atrial Fibrillation, and noisy. If the period includes 2 windows and $Y_1$=[0.1 0.6 0.3] with $w_1$=0.3, and $Y_2$=[0.1 0.3 0.6] with $w_2$=0.7, the final output from the attention model or score ($Y_{attention}$) can be calculated as follows: 0.3×[0.1 0.6 0.3]+ 0.7×[0.1 0.3 0.6]. The score ($Y_{attention}$) may then equal [0.1000 0.39 0.51]. Based on that score, the system may determine that period is associated most likely with the class "noisy" (corresponding to probability of 0.51).

Computer System

One or more of the devices and/or systems of the system 100 may be and/or include a computer system and/or device. FIG. 8 is a block diagram showing an example of a computer system 800. The modules of the computer system 800 may be included in at least some of the systems and/or modules, as well as other devices and/or systems of the system 100.

The system for carrying out the embodiments of the methods disclosed herein is not limited to the systems shown in FIGS. 1 and 8. Other systems may also be used. It is also to be understood that the system 800 may omit any of the modules illustrated and/or may include additional modules not shown.

The system 800 shown in FIG. 8 may include any number of modules that communicate with each other through electrical or data connections (not shown). In some embodiments, the modules may be connected via any network (e.g., wired network, wireless network, or a combination thereof).

The system 800 may be a computing system, such as a workstation, computer, or the like. The system 800 may include one or more processors 812. The processor(s) 812 may include one or more processing units, which may be any known processor or a microprocessor. For example, the processor(s) may include any known central processing unit (CPU), graphical processing unit (GPU) (e.g., capable of efficient arithmetic on large matrices encountered in deep learning models), among others, or any combination thereof. The processor(s) 812 may be coupled directly or indirectly to one or more computer—readable storage media (e.g., memory) 814. The memory 814 may include random access memory (RAM), read only memory (ROM), disk drive, tape drive, etc., or a combinations thereof. The memory 814 may be configured to store programs and data, including data structures. In some embodiments, the memory 814 may also include a frame buffer for storing data arrays.

In some embodiments, another computer system may assume the data analysis or other functions of the processor(s) 812. In response to commands received from an input device, the programs or data stored in the memory 814 may be archived in long term storage or may be further processed by the processor and presented on a display.

In some embodiments, the system 800 may include a communication interface 816 configured to conduct receiving and transmitting of data between other modules on the system and/or network. The communication interface 816 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 810 may include an input/output interface 818 configured for receiving information from one or more input devices 820 (e.g., a keyboard, a mouse, and the like) and/or conveying information to one or more output devices 820 (e.g., a printer, a CD writer, a DVD writer, portable flash memory, etc.). In some embodiments, the one or more input devices 820 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIGS. 2 and 3) may be implemented using software applications that are stored in a memory and executed by the one or more processors (e.g., CPU and/or GPU) provided on the system 100. In some embodiments, the disclosed methods may be implemented using software applications that are stored in memories and executed by the one or more processors distributed across the system.

As such, any of the systems and/or modules of the system 100 may be a general purpose computer system, such as system 800, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 8. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A computer-implemented method for using machine learning to determine abnormal cardiac activity of a subject, the method comprising:

receiving one or more periods of time of cardiac data for a subject from one or more cardiac sensors of a wearable device and motion data for the subject from one or more motion sensors of the wearable device, each period of time including more than one window of the cardiac data and the motion data;

determining one or more signal quality indices for the cardiac data and for the motion data for each window of the cardiac data and the motion data of the one or more periods of time;

extracting one or more cardiovascular features for each period of time using at least the cardiac data, the motion data, and the one or more signal quality indices for the cardiac data and the motion data;

applying a tensor transform to the cardiac data and/or the motion data to generate a tensor for each window of the one or more periods of time;

applying a trained deep learning architecture to each tensor of the one or more periods of time to classify each window and/or each period into one or more classes using at least the one or more signal quality indices for the cardiac data and the motion data and cardiovascular features;

the deep learning architecture including a convolutional neural network, a bidirectional recurrent neural network, and an attention network;

the one or more classes including abnormal cardiac activity and normal cardiac activity; and generating a report including a classification of cardiac activity of the subject for the one or more periods based on the one or more classes.

2. The method according to claim 1, further comprising:
receiving subject contextual information for the subject, the subject contextual information including medical history and demographic information;
wherein the extracting uses one or more subject information features related to the subject contextual information to extract one or more cardiovascular features for each period of time, and the trained deep learning architecture uses the one or more subject information features to classify the cardiac activity for each window of the period.

3. The method according to claim 1, wherein:
the one or more cardiac sensors includes a photoplethysmogram (PPG) sensor and the one or more motion sensors includes an accelerometer; and
the tensor transform is applied to the cardiac data and the motion data for each window.

4. The method according to claim 3, wherein the one or more signal quality indices for the cardiac data are determined using more than one beat detector and the one or more quality indices for the motion data are determined based on energy, the method further comprising:
determining a quality channel for each window based on the one or more signal quality indices for the cardiac data and the motion data, the quality channel corresponding to a channel in each window having the one more quality indices that is higher than remaining channels in each window;
wherein the one or more cardiovascular features are extracted for the quality channel of each window.

5. The method according to claim 1, wherein the applying the deep learning architecture includes:
encoding each tensor for each window of the one or more periods using the deep convolutional network into one or more deep learning features associated with cardiac activity;
applying the bidirectional recurrent network to determine a probability that each window of the one or more periods belongs to a class of the one or more classes, the bidirectional recurrent network using the one or more deep learning features, the one more signal quality indices for the cardiac data and/or the motion data, and/or one or more cardiovascular features to classify each window of the one or more periods; and
determining the classification of cardiac activity for each window of the one or more periods and/or each period by applying the attention network to the probability for each window of the one or more periods.

6. The method according to claim 5, wherein the attention network determines a score for each window and/or each period, the score representing the classification of cardiac activity.

7. The method according to claim 6, wherein when the classification of cardiac activity includes abnormal cardiac activity, a window of each period having a highest score represents the window including the abnormal cardiac activity.

8. A non-transitory computer-readable storage medium storing instructions for using machine learning to determine abnormal cardiac activity of a subject, the instructions comprising
receiving one or more periods of time of cardiac data for a subject from one or more cardiac sensors of a wearable device and motion data for the subject from one or more motion sensors of the wearable device, each period of time including more than one window of the cardiac data and the motion data;
determining one or more signal quality indices for the cardiac data and for the motion data for each window of the cardiac data and the motion data of the one or more periods of time;
extracting one or more cardiovascular features for each period of time using at least the cardiac data, the motion data, and the one or more signal quality indices for the cardiac data and the motion data;
applying a tensor transform to the cardiac data and/or the motion data to generate a tensor for each window of the one or more periods of time;
applying a trained deep learning architecture to each tensor of the one or more periods of time to classify each window and/or each period into one or more classes using at least the one or more signal quality indices for the cardiac data and the motion data and cardiovascular features;
the deep learning architecture including a convolutional neural network, a bidirectional recurrent neural network, and an attention network;
the one or more classes including abnormal cardiac activity and normal cardiac activity; and
generating a report including a classification of cardiac activity of the subject for the one or more periods based on the one or more classes.

9. The medium according to claim 8, the instructions further comprising:
receiving subject contextual information for the subject, the subject contextual information including medical history and demographic information;
wherein the extracting uses one or more subject information features related to the subject contextual information to extract one or more cardiovascular features for each period of time, and the trained deep learning architecture uses the one or more subject information features to classify the cardiac activity for each window of the period.

10. The medium according to claim 8, wherein:
the one or more cardiac sensors includes a photoplethysmogram (PPG) sensor and the one or more motion sensors includes an accelerometer; and
the tensor transform is applied to the cardiac data and the motion data for each window.

11. The medium according to claim 10, wherein the one or more signal quality indices for the cardiac data are determined using more than one beat detector and the one or more quality indices for the motion data are determined based on energy, the method further comprising:
determining a quality channel for each window based on the one or more signal quality indices for the cardiac data and the motion data, the quality channel corresponding to a channel in each window having the one more quality indices that is higher than remaining channels in each window;
wherein the one or more cardiovascular features are extracted for the quality channel of each window.

12. The medium according to claim 8, wherein the applying the deep learning architecture includes:
encoding each tensor for each window of the one or more periods using the deep convolutional network into one or more deep learning features associated with cardiac activity;
applying the bidirectional recurrent network to determine a probability that each window of the one or more periods belongs to a class of the one or more classes, the bidirectional recurrent network using the one or more deep learning features, the one more signal quality indices for the cardiac data and/or the motion data, and/or one or more cardiovascular features to classify each window of the one or more periods; and determining the classification of cardiac activity for each window of the one or more periods and/or each period by applying the attention network to the probability for each window of the one or more periods.

13. The medium according to claim 12, wherein:

the attention network determines a score for each window and/or each period, the score representing the classification of cardiac activity; and when the classification of cardiac activity includes abnormal cardiac activity, a window of each period having a highest score represents the window including the abnormal cardiac activity.

14. A system for using machine learning to determine abnormal cardiac activity of a subject, comprising:

a wearable device, the wearable device including:
  one or more cardiac sensors configured to collect cardiac data; and
  one or more motion sensors configured to collect motion data;

a cardiac activity processing device, the cardiac activity processing device including:
  a memory; and
  one or more processors, wherein the one or more processors is configured to cause:
    receiving one or more periods of time of the cardiac data for a subject from one or more cardiac sensors of a wearable device and the motion data for the subject of from one or more motion sensors of the wearable device, each period of time including more than one window of the cardiac data and the motion data;
    determining one or more signal quality indices for the cardiac data and for the motion data for each window of the cardiac data and the motion data of the one or more periods of time;
    extracting one or more cardiovascular features for each period of time using at least the cardiac data, the motion data, and the one or more signal quality indices for the cardiac data and the motion data;
    applying a tensor transform to the cardiac data and/or the motion data to generate a tensor for each window of the one or more periods of time;
    applying a trained deep learning architecture to each tensor of the one or more periods of time to classify each window and/or each period into one or more classes using at least the one or more signal quality indices for the cardiac data and the motion data and cardiovascular features;
    the deep learning architecture including a convolutional neural network, a bidirectional recurrent neural network, and an attention network;
    the one or more classes including abnormal cardiac activity and normal cardiac activity; and
    generating a report including a classification of cardiac activity of the subject for the one or more periods based on the one or more classes.

15. The system according to claim 14, wherein the processor is further configured to cause:

receiving subject contextual information for the subject, the subject contextual information including medical history and demographic information;

wherein the extracting uses one or more subject information features related to the subject contextual information to extract one or more cardiovascular features for each period of time, and the trained deep learning architecture uses the one or more subject information features to classify the cardiac activity for each window of the period.

16. The system according to claim 14, wherein:

the one or more cardiac sensors includes a photoplethysmogram (PPG) sensor, and the one or more motion sensors includes an accelerometer; and the tensor transform is applied to the cardiac data and the motion data for each window.

17. The system according to claim 16, wherein:

the one or more signal quality indices for the cardiac data are determined using more than one beat detector;

the one or more quality indices for the motion data are determined based on energy; and the processor is further configured to cause:
  determining a quality channel for each window based on the one or more signal quality indices for the cardiac data and the motion data, the quality channel corresponding to a channel in each window having the one more quality indices that is higher than remaining channels in each window;

wherein the one or more cardiovascular features are extracted for the quality channel of each window.

18. The system according to claim 14, wherein the applying the deep learning architecture includes:

encoding each tensor for each window of the one or more periods using the deep convolutional network into one or more deep learning features associated with cardiac activity;

applying the bidirectional recurrent network to determine a probability that each window of the one or more periods belongs to a class of the one or more classes, the bidirectional recurrent network using the one or more deep learning features, the one more signal quality indices for the cardiac data and/or the motion data, and/or one or more cardiovascular features to classify each window of the one or more periods; and determining the classification of cardiac activity for each window of the one or more periods and/or each period by applying the attention network to the probability for each window of the one or more periods.

19. The system according to claim 18, wherein the attention network determines a score for each window and/or each period, the score representing the classification of cardiac activity.

20. The system according to claim 19, wherein when the classification of cardiac activity includes abnormal cardiac activity, a window of each period having a highest score represents the window including the abnormal cardiac activity.

* * * * *